(12) United States Patent
Tung et al.

(10) Patent No.: US 6,313,359 B1
(45) Date of Patent: Nov. 6, 2001

(54) METHOD OF MAKING HYDROFLUOROCARBONS

(75) Inventors: Hsueh Sung Tung, Erie County, NY (US); Robert Scott Wedinger, Morris County, NJ (US)

(73) Assignee: Honeywell International Inc., Morris Township, NJ (US)

( * ) Notice: Subject to any disclaimer, the term of this patent is extended or adjusted under 35 U.S.C. 154(b) by 0 days.

(21) Appl. No.: 09/617,634

(22) Filed: Jul. 17, 2000

(51) Int. Cl.⁷ .................................................... C07C 19/08
(52) U.S. Cl. ............................................................. 570/142
(58) Field of Search ................................................ 570/142

(56) References Cited

U.S. PATENT DOCUMENTS

| 5,395,997 | 3/1995 | VanDerPuy et al. | 570/167 |
| 5,574,192 | 11/1996 | VanDerPuy et al. | 570/167 |
| 5,728,904 | 3/1998 | VanDerPuy et al. | 570/176 |

FOREIGN PATENT DOCUMENTS

WO9414736   7/1994   (WO) .

*Primary Examiner*—Alan Siegel
(74) *Attorney, Agent, or Firm*—Colleen D. Szuch

(57) ABSTRACT

A method of producing hydrofluorocarbons and methods of producing other commercially attractive compounds formed as by-products of hydrofluorocarbon production by using aldehydes as a principal reactant.

37 Claims, No Drawings

METHOD OF MAKING HYDROFLUOROCARBONS

FIELD OF THE INVENTION

The present invention relates to new methods for making hydrofluorocarbons (HFC's).

BACKGROUND OF THE INVENTION

HFCs are of particular interest as potential replacements for highly useful chlorofluorocarbons (CFCs) and hydrochlorofluorocarbons (HCFCs). Unlike CFCs and HCFCs, HFCs do not contain chlorine and therefore do not decompose to form chlorine-containing chemical species, which are suspected of causing depletion of the ozone layer. While HFCs thus avoid the main disadvantage of such chlorine-containing compounds, they nevertheless possess many of the beneficial properties of those compounds. For example, HFCs have been used successfully in place of HCFCs and CFCs as heat transfer agents, blowing agents, and propellants. Thus, HFCs are desirable targets of chemical synthesis.

Known methods for forming HFC's generally use as starting materials halogenated alkanes and alkenes, such as, for example, vinylidene chloride, carbon tetrachloride and perchloroethylene. For example, U.S. Pat. No. 5,574,192—Van Der Puy et al discloses a method of making 1,1,1,3,3-pentafluoropropane (HFC-245fa) in which vinyl chloride is reacted with carbon tetrachloride and then fluorinated to produce the desired HFC. U.S. Pat. No. 5,728,904—Van Der Puy et al discloses a three-step method of reacting carbon tetrachloride with vinylidene chloride, fluorinating and then reducing to make the desired HFC.

The present inventors have come to appreciate that such prior processes are disadvantageous for several reasons. One such disadvantage is that the availability of many halogenated compounds, such as carbon tetrachloride, is limited and their use as starting materials tends to be very expensive. Another disadvantage is that these prior art processes are not flexible and produce HFC-245fa as the sole product. No useful intermediates or by-products are co-produced. Thus, the HFC-245fa produced by the prior art processes have relatively high operating costs, as well as relatively high capital costs.

Recognizing these and other drawbacks of the prior art, the present inventors have perceived a need for a new, efficient and more desirable method for producing a wide range of HFCs. These and other objects are achieved by the present invention as described below.

DESCRIPTION OF THE INVENTION AND PREFERRED EMBODIMENTS

The present invention is directed to a method of producing hydrofluorocarbons (HFCs) and to methods of producing other commercially attractive compounds which are produced as by-products of the inventive process. An important aspect of the invention is the discovery that HFCs can be advantageously produced using aldehydes as a principal reactant. Although it is contemplated that aldehydes in general will provide the advantages of the present invention, particularly preferred aldehydes are illustrated in Formula I below:

$$H_aX_bC\text{—}C(O)\text{—}H \quad (I)$$

wherein, a+b=3 and each X is a halogen or other chemical moiety replaceable by chlorine such as, for example, hydroxyl, alkoxy, acetate, amino, thio or phosphorus groups.

A large number of aldehydes in accordance with Formula I, are commercially available, including, for example, acetaldehyde, diacetate acetaldehyde and the like. In addition, a number of aldehyde derivatives, which can be used to form readily aldehydes for use in the present invention, are commercially available, including, for example, dimethyl acetal, hemiacetal and the like. Furthermore, many compounds of Formula I are known in the literature and are obtainable by art-recognized procedures.

Applicants have discovered that aldehydes as a class of compounds can be used with great advantage in a process which comprises converting the aldehyde, and preferably an aldehyde in accordance with Formula I, to a hydrofluorocarbon. Applicants have discovered that a process which utilizes such a conversion operation is highly advantageous in at least two respects. First, the cost of producing HFC's according to the present aldehyde conversion operation is greatly reduced relative to conventional HFC production techniques. Second, the preferred form of the present aldehyde conversion process can be adapted to also produce valuable by-products that enhance the overall desirability of the process.

According to preferred embodiments of the present invention, the step of converting the aldehyde to an HFC comprises the steps of: (a) chlorinating the aldehyde, preferably acetaldehyde, to produce a chlorinated aldehyde; and (b) converting said chlorinated aldehyde to an HFC. Preferably, the chlorinating step produces a highly-chlorinated aldehyde, and even more preferably a fully-chlorinated aldehyde, that is, an aldehyde molecule wherein the aldehyde functionality (CHO) remains intact but the carbon chain extending therefrom is perchlorinated. As used herein, the term "highly-chlorinated aldehyde" refers generally to an aldehyde in which the carbon chain extending from the aldehyde functionality is at least 65% chlorinated, wherein the percentage refers to the relative degree of chlorination, with 100% being perchlorination of the extending carbon chain.

Although applicants do not wish to be bound by or to any particular theory of operation, it is believed that the methods according to the preferred aspects of the present invention involve the reaction steps shown below.

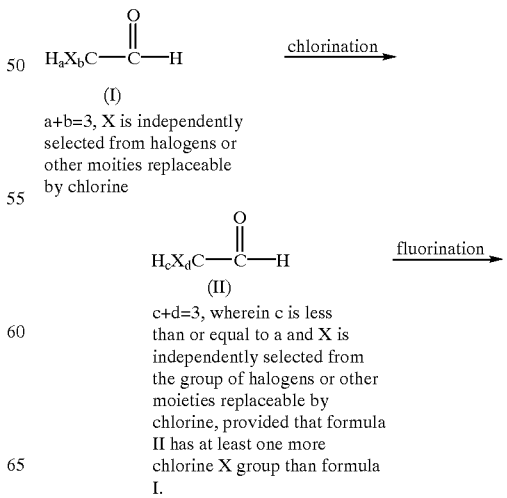

-continued

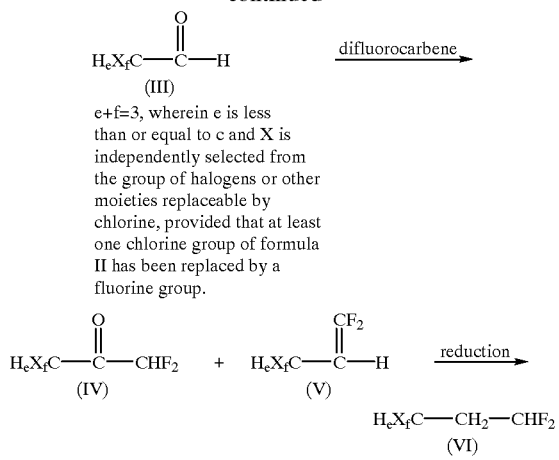

e+f=3, wherein e is less than or equal to c and X is independently selected from the group of halogens or other moieties replaceable by chlorine, provided that at least one chlorine group of formula II has been replaced by a fluorine group.

The aldehyde chlorination step preferably comprises reacting the aldehyde with a chlorinating agent under conditions effective to achieve chlorination of at least a portion of the aldehyde in the reactant stream, and preferably a substantial portion of the aldehyde in the reactant stream. It is contemplated that, in view of the teachings contained herein, those skilled in the art will be able to readily select suitable chlorinating agents for use with any particular aldehyde or mixture of aldehydes as well as the conditions effective for obtaining the desired results. In general, a suitable chlorinating agent is any material capable of providing chlorine in the reaction, including elemental chlorine, elemental chlorine diluted with inert gases, such as nitrogen or helium, metallic chloride, hydrochloric acid ("HCl"), HCl and oxygen mixtures, HCl and air mixtures, and hypochlorides. A preferred chlorinating agent comprises elemental chlorine.

Those skilled in the art will appreciate that the amount of chlorinating agent to be used according to the present process will depend on many variables, including the particular aldehyde being chlorinated, the degree of chlorination desired and the desired yield from the chlorination reaction. Preferably, the amount of chlorinating agent used is an amount effective to achieve a greater than 90% conversion of the aldehyde starting material to fully-chlorinated aldehyde. For example, in certain preferred processes in which the aldehyde is acetaldehyde and the fully-chlorinated aldehyde is trichloroacetaldehyde, the mole ratio of aldehyde starting material to elemental chlorine is preferably from about 1:3 to about 1:12, more preferably from about 1:4 to about 1:10 and even more preferably from about 1:5 to about 1:8.

According to preferred embodiments of the present process, the aldehyde is reacted with a chlorinating agent to produce a stream comprising chlorinated aldehydes. In such embodiments, one or more reactant streams comprising an aldehyde and a chlorinating agent are reacted to produce a stream containing chlorinated aldehydes. The reactants can be fed individually or as a mixture to a chlorination reactor, or diluted with inert material, such as nitrogen or argon, or perchlorinated material. Once the reaction is under way, the reactants may be continuously added under pressure to supply the additional amounts of reactants needed to continue the process.

As desired, one or more of the reactants comprising the chlorination agent and the aldehyde may be preheated in at least one vaporizer before being feed to the reactor. The term "preheating" refers to vaporizing and optionally superheating the reactants. Suitable temperatures for preheating range from about 30° C. to about 300° C., preferably from about 50° C. to about 200° C. The vaporizer, as well as other vessels used in this process, may be made of any suitable corrosion resistant material.

Those skilled in the art will appreciate that the conditions under which the chlorination reaction occurs, including the pressure, temperature and period of reaction, will depend on numerous factors, including the particular starting materials used and the chlorinated aldehydes which are desired. In view of the teachings contained herein, those skilled in the art will be able to select the appropriate reaction conditions to achieve the particular desired result. For preferred embodiments in which the aldehyde reactant is acetaldehyde and the desired chlorinated aldehyde is trichloroacetaldehyde, the chlorination reaction is preferably carried out at temperatures of from about 50° C. to about 400° C., more preferably from about 80° C. to about 325° C., and even more preferably from about 100° C. to about 250° C. Reaction pressure is not believed to be critical, but the reaction preferably takes place in superatmospheric pressures.

In many embodiments, the chlorinated aldehyde stream produced in the chlorination reaction will comprise not only the chlorinated aldehydes, but also by-products and impurities. As an optional step, the aldehydes which have been chlorinated to the desired extent may be separated from this stream by conventional means, such as distillation. Optionally, but preferably, aldehydes that have not been chlorinated to the desired extent and/or unreacted starting material recovered from such a separation step are recycled to the reactor for further reaction. Recycling such under-chlorinated aldehydes and unreacted starting material generally results in higher overall yields and selectivity of the desired chlorination reaction.

As mentioned above, the present invention also preferably comprises the step of converting the chlorinated aldehyde to an HFC. This chlorinated aldehyde conversion step preferably comprises the steps of: (i) fluorinating the chlorinated aldehyde to form a fluorinated aldehyde; and (ii) converting said fluorinated aldehyde to an HFC. Preferably, the fluorinating step produces a highly-fluorinated aldehyde, and even more preferably a fully-fluorinated aldehyde, that is, a substantially per-fluorinated aldehyde. The term "highly-fluorinated aldehyde" refers to a aldehyde in which the carbon chain extending from the aldehyde functionality is at least 65% fluorinated, wherein the percentage refers to the degree of fluorination, with 100% being per-fluorination. The fluorination step preferably comprises reacting the chlorinated aldehyde with a fluorinating agent in the presence of a fluorination catalyst. In preferred embodiment, the fluorination reaction is carried out in a reactor vessel to produce a fluorinated aldehyde stream.

In general, suitable fluorination agents includes any material capable of providing fluorine to the reaction. Examples of suitable fluorinating agents are substantially anhydrous hydrogen fluoride, aqueous hydrogen fluoride, metal fluorides, halogen fluorides, elemental fluorine and sulfur fluorides. A preferred fluorination agent is substantially anhydrous hydrogen fluoride (HF). Anhydrous hydrogen fluoride is preferred because the presence of water in the reaction tends to deactivate the fluorination catalyst. The term "substantially anhydrous", as used herein, means that the HF contains less than about 0.05 weight percent water and preferably contains less than about 0.02 weight percent water. It should be understood, however, that the presence of water in the catalyst can be compensated for by increasing the amount of catalyst used.

Preferably, the amount of fluorinating agent used is an amount effective to achieve a greater than 90% conversion of chlorinated aldehyde to fluorinated aldehyde. For example, in particularly preferred embodiments in which the chlorinated aldehyde comprises trichloroacetaldehyde and the fluorinated aldehyde comprises trifluoroacetaldehyde, the mole ratio of chlorinated aldehyde to HF is preferably from about 1:20, more preferably from about 1:12, and even more preferably from about 1:7.

As desired, one or more of the reactants comprising the fluorination agent and the chlorinated aldehyde may be preheated in at least one vaporizer before feeding the reactor. Suitable temperatures for preheating range from about 125° C. to about 400° C., preferably from about 150° C. to about 350° C., and more preferably from about 175° C. to about 275° C.

The fluorination reactor is charged preferably with a fluorination catalyst before feeding the reactants to the reactor. The fluorination catalyst preferably comprises an inorganic metal catalyst which promotes a reaction involving the substitution of fluorine for chlorine in a chlorinated organic molecule. Numerous fluorination catalysts are known to those skilled in the art. Exemplary catalysts include, without limitation, chromium, copper, aluminum, cobalt, magnesium, manganese, zinc, nickel and iron oxides, hydroxides, halides, oxyhalides and inorganic salts thereof, Cr2O3/Al2O3, Cr2O3/AlF3, Cr2O3/carbon, CoCl2CrO3/Al2O3, NiCl2/Cr2O3/Al2O3, CoCl2AlF3 and NiCl2/AlF3. Additionally, supported metal catalysts such as nickel, cobalt, zinc, iron, and copper supported on chromia, magnesia, or alumina may be used. Such chromium oxide/aluminum oxide catalysts are known and are described, for example, in U.S. Pat. No. 5,155,082, which is incorporated herein by reference. Preferably, chromium oxide ($Cr_2O_3$), a commercially available catalyst, is used.

Before adding the reactants to the fluorination reactor, it may be preferable to pretreat the catalyst chemically and/or physically to create active sites which facilitate fluorination. For example, the catalyst can be pretreated by calcining it under a flow of inert gas, such as nitrogen, at a temperature comparable to or higher than that of the fluorination reaction. Next, the calcined catalyst is exposed to a fluorinating agent alone or in combination with up to about 5 to about 99 weight percent of inert gas at a temperature from about 25° C. to about 450° C. for at least about an hour.

The amount of catalyst used can vary widely and can be determined by one skilled in the art without undue experimentation. The amount depends on a number of factors including the catalyst employed, reactants and other process variables. In a batch process, the mole ratio of chlorinated aldehyde to catalyst used is preferably no less than about 1:1, more preferably no less than about 2:1, and even more preferably no less than about 10:1.

The reactants can be fed individually or as a mixture to the reactor, or diluted with inert material, such as nitrogen or argon, or perhalogenated material. Once the reaction is underway, the reactants may be continuously added under pressure to supply the additional amounts of reactants needed to continue the process.

The temperature at which the fluorination reaction is conducted and the period of reaction will depend on the starting materials, amounts used, and catalyst used. In view of the present teachings, those skilled in the art will be able to adapt the reaction parameters to achieve the particular desired results for numerous starting materials and desired HFCs. For methods involving the use of trichloroacetaldehyde as the chlorinated aldehyde, temperatures in the fluorination reactor are preferably from about 125° C. and about 425° C., more preferably from about 200° C. to about 375° C., and even more preferably from about 275° C. and about 350° C. Pressure is not critical. Atmospheric, sub- or super-atmospheric pressures can be used.

In a continuous process, the contact time for the reactants stream is from about 1 to about 300 seconds, preferably from about 5 to about 200 seconds, and more preferably from about 10 to about 120 seconds.

In many embodiments, the fluorinated aldehyde stream produced in the fluorination reaction will comprise not only fluorinated aldehydes, but also by-products and impurities. As an optional step, at least a portion of the fully-fluorinated aldehyde may be separated from the fluorinated aldehyde stream via conventional purification means, such as distillation. As a further optional step, any aldehyde recovered from the fluorinated aldehyde stream may be recycled back to the reactor for further fluorination.

The preferred methods of the present invention also comprise converting fully- fluorinated aldehyde to an HFC. While applicants contemplate that the teachings contained herein will enable those skilled in the art to adapt various fluorinated aldehyde conversion techniques for use with the present invention, it is preferred that conversion of the fluorinated aldehyde to an HFC comprises the steps of: (a) reacting the fluorinated aldehyde with a difluorocarbene to form a carbene-reaction product; and (b) converting at least a portion of the carbene-reaction product to an HFC.

Although applicants do not wish to be bound by or to any particular theory of operation, it is believed that the carbene-reaction product formed by reacting the fluorinated aldehyde with difluorocarbene comprises a highly-fluorinated ketone, a highly-fluorinated alkene or a mixture thereof. The term "highly-fluorinated ketone" refers generally to a ketone in which the carbon chains surrounding the ketone functionality are at least 80% fluorinated, wherein the percentage refers to the degree of fluorination, with 100% being perfluorination. The term "highly-fluorinated alkene" refers generally to an alkene in which the carbon chain is at least 80% fluorinated, wherein the percentage refers to the degree of fluorination, with 100% being a perfluorinated alkene.

Highly-fluorinated ketones and highly fluorinated alkenes are both desirable products of the carbene reaction because they can be converted to HFCs according to the present invention. In certain embodiments of the present invention, it may be desirable to produce or isolate only a highly-fluorinated ketone or a highly-fluorinated alkene, however, in preferred embodiments, a mixture of ketones and alkenes can be used. Accordingly, the term "carbene-reaction product"as used herein, refers generally to a product comprising either a highly-fluorinated ketone or highly-fluorinated alkene alone, or a mixture of highly-fluorinated ketones and alkenes.

The carbene-reaction step preferably comprises reacting the fluorinated aldehyde with a difluorocarbene. In preferred embodiment, the carbene reaction step is carried out in a reactor vessel to produce a carbene reaction product.

In general, suitable difluorocarbene agents include materials capable of providing to the reaction a difluorocarbene species which reacts with the fluorinated aldehyde to produce a carbene-reaction product. Preferred difluorocarbene agents include chlorodifluoromethane, trifluoromethane and the like. A particularly preferred difluorocarbene agent comprises chlorodifluoromethane.

Those skilled in the art will appreciate that the amount of difluorocarbene agent to be used according to the present invention will depend on many variables, including the particular aldehyde being used as starting material and the desired yield from the carbene reaction. Preferably, the amount of difluorocarbene agent used is an amount effective to achieve a greater than 90% conversion of the fluorinated aldehyde to a carbene-reaction product. For preferred processes in which the fluorinated aldehyde comprises trifluoroacetaldehyde, the mole ratio of fluorinated aldehyde to chlorodifluoromethane is from about 5:1, preferably from about 3:1, and more preferably from about 1:1.

As desired, one or more of the reactants comprising the difluorocarbene agent and the fluorinated aldehyde may be preheated in at least one vaporizer before feeding the reactor. Suitable temperatures for preheating range from about 25° C. to about 800° C., preferably from about 100° C. to about 500° C., and more preferably from about 200° C. to about 400° C.

The reactants can be fed individually or as a mixture to the reactor. Once the reaction is underway, the reactants may be continuously added under pressure to supply the additional amounts of reactants needed to continue the process.

The temperature at which the carbene reaction is conducted and the period of reaction will depend in part on the starting materials and amounts used. In view of the present teachings, those skilled in the art will be able to adapt the reaction parameters to achieve the particular desired results for numerous starting materials and desired HFCs. For methods involving the use of fluoroacetaldehyde as the fluorinated aldehyde, temperatures in the carbene reactor are preferably from about 125° C. and about 475° C., more preferably from about 200° C. to about 425° C., and even more preferably from about 275° C. and about 375° C. Reaction pressure is not believed to be critical, but the reaction preferably takes place at superatmospheric pressure.

In many embodiments, the carbene-reaction product stream produced in the carbene reaction will comprise not only carbene-reaction products, but also by-products and impurities. As an optional step, at least a portion of a desired carbene-reaction product may be separated from the fluorinated ketone stream via conventional purification means, such as distillation. As a further optional step, any aldehyde recovered from the fluorinated ketone stream may be recycled back to the reactor for further carbene reaction.

As mentioned above, the preferred methods of the present invention comprise converting carbene-reaction product to HFC. While applicants contemplate that the teachings contained herein will enable those skilled in the art to adapt various carbene-reaction product conversion techniques for use with the present invention, it is preferred that the carbene-reaction product conversion step comprises reducing a carbene-reaction product to an HFC.

In a preferred embodiment, the reduction step of the present invention comprises reacting the carbene-reaction product with hydrogen in the presence of a catalyst to reduce the carbene reaction product to an HFC. In a preferred embodiment, the reduction reaction is carried out in a reactor vessel to produce a stream containing the HFC. In general, suitable sources of hydrogen for the reduction reaction include any material capable of providing hydrogen to the reaction. A preferred source of hydrogen is elemental hydrogen.

Preferably, the amount of hydrogen used is an amount effective to achieve a greater than 90% conversion of the carbene-reaction product, including any recycled carbene-reaction product, to the corresponding HFC. For embodiments in which carbene-reaction product comprises a mixture of pentafluoroacetone and pentafluoropropene, the mole ratio of carbene-reaction product to hydrogen is preferably about 1:10 or greater, more preferably about 1:5, and even more preferably about 1:3.

The reduction reactor is charged preferably with a reduction catalyst before feeding the reactants to the reactor. The term "reduction catalyst" as used herein refers to an inorganic metal catalyst which promotes a reaction involving the conversion of a molecule having a carbonyl moiety and/or a molecule having an unsaturated double bond to a saturated organic molecule. Such reduction catalysts include, for example, oxides, hydroxides, halides, oxyhalides and inorganic salts of metals, not limited to, platinum, palladium, nickel, and ruthenium. Additionally, supported metal catalysts such as palladium supported on carbon (Pd/C) or palladium supported on alumina (Pd/$Al_2O_3$) can be used. Preferably, Pd/C catalyst is used.

As desired, the carbene-reaction product may be preheated in at least one vaporizer before feeding same to the reduction reactor. Suitable temperatures for preheating range from about 25° C. to about 400° C., preferably from about 100° C. to about 200° C.

The temperature and pressure at which the reaction is conducted and the period of reaction will depend on the starting materials and amounts used. In view of the present teachings, those skilled in the art will be able to adapt the reaction parameters to achieve the particular desired results for numerous starting materials and desired HFCs. For methods involving the use of a mixture of pentafluoroacetone and pentafluoropropene as the carbene-reaction product, temperatures in the reduction reactor are preferably from about 25° C. to about 400° C., more preferably from about 50° C. to about 300° C., and even more preferably from about 100° C. and about 200° C. For such embodiments, the reactor pressure is preferably from about 1 to about 400 atmospheres (atm), more preferably from about 5 to about 300 atm, and still more preferably from about 10 to about 200 atm.

Products produced in accordance with the present invention find particular utility as replacements for fluorocarbons, chlorofluorocarbons and hydrochlorofluorocarbons in a wide variety of applications. For example, the products of the present invention can be used as aerosols, refrigerants, blowing agents, and fire-extinguisher compounds.

EXAMPLE 1

In order to illustrate, in a non-limiting manner, the present invention is described in connection with the following example, which describes the preparation of 1,1,1,3,3-pentafluoropropane from acetaldehyde.

To an Inconel alloy vapor phase plug flow reactor packed with nickel mesh and having the dimensions of ½' by 3' is fed 1 g/min of acetaldehyde and 10 g/min of elemental chlorine to react at about 250° C. at atmospheric pressure. An in-line gas chromatograph is equipped to take on-line samples periodically.

Analysis of on-line samples indicates formation of trichloroacetaldehyde in about 60% single-pass selectivity as well as lesser-chlorinated acetaldehyde products. The lesser-chlorinated acetaldehydes are separated from the trichloroacetaldehyde via distillation and are recycled back into the vapor phase plug flow reactor for making more trichloroacetaldehyde. The overall selectivity is about 90%.

Subsequently, 100 ml of chromium oxide ($Cr_2O_3$) catalyst is packed in a vapor phase reactor having dimensions similar to those of the aforementioned plug flow reactor. This catalyst is then heat-treated at 375° C. in 1 L/min nitrogen for 16 hours, followed by hydrogen fluoride ("HF") treatment at 350° C. for 4 hours. The HF flow rate is 1 ml/min in 250 ml/min nitrogen.

After catalyst pre-treatment is completed, 43 g/hr trichloroacetaldehyde and 45 g/hr anhydrous HF are fed to the reactor. The reaction is conducted at atmospheric pressure and a temperature of about 325° C. An in-line gas chromatograph is equipped to take on-line samples periodically.

Analysis of on-line samples indicates formation of trifluoroacetaldehyde is greater than 60% single-pass selectivity as well as lesser-fluorinated acetaldehyde products. The lesser-fluorinated acetaldehydes are separated from the trifluoroacetaldehyde via distillation and are recycled back into the vapor phase plug flow reactor for making more trifluoroacetaldehyde. The overall selectivity is about 90%.

Next, 50 g/hr of trifluoroacetaldehyde and 50 g/hr of chlorodifluoromethane are fed simultaneously into a vapor phase reactor, having dimensions similar to those of the aforementioned plug flow reactor, packed with nickel mesh. The reaction is conducted at atmospheric pressure and a temperature of 350° C. Effluents from the reactor are analyzed using an in-line gas chromatograph.

Analysis of on-line samples indicates selectivity of the combined pentafluoroacetone and pentafluoropropene is about 60%. The unreacted trifluoroacetaldehydes are separated from the pentafluoroacetone and pentafluoropropene mixture via distillation and are recycled back into the vapor phase plug flow reactor for making more pentafluoroacetone and pentafluoropropene. The overall selectivity is about 85%.

Approximately 100 cc of Pd/C. catalyst is then packed into a ½' diameter pipe reactor. Approximately 1 g/min of the pentafluoroacetone and pentafluoropropene mixture and 500cc/min hydrogen gas is fed into the reactor at 10 atm and 180° C. 1,1,1,3,3-pentafluoropropane is produced in greater than 90% yield.

Having thus described a few particular embodiments of the invention, various alterations, modifications and improvements will readily occur to those skilled in the art. Such alterations, modifications and improvements as are made obvious by this disclosure are intended to be part of this description though not expressly stated herein, and are intended to be within the spirit and scope of the invention. Accordingly, the foregoing description is by way of example only, and not limiting. The invention is limited only as defined in the following claims and equivalents thereto.

What is claimed is:

1. A method for the preparation of a hydrofluorocarbon comprising the steps of:
   (a) chlorinating an aldehyde to produce a chlorinated aldehyde;
   (b) fluorinating said chlorinated aldehyde to produce a fluorinated aldehyde;
   (c) reacting said fluorinated aldehyde with difluorocarbene to produce a carbene-reaction product; and
   (d) reducing said carbene-reaction product to produce a hydrofluorocarbon.

2. The method of claim 1, wherein the chlorination step (a) produces a product stream comprising a mixture of fully-chlorinated aldehyde and partially-chlorinated aldehydes.

3. The method of claim 2, further comprising the steps of separating at least a portion of said partially-chlorinated aldehydes from said product stream and recycling said separated portion of said partially-chlorinated aldehydes to said chlorinating step (a).

4. The method of claim 1, wherein the fluorination step (b) produces a product stream comprising a mixture of fully-fluorinated aldehyde and partially-fluorinated aldehydes.

5. The method of claim 4, further comprising the steps of separating at least a portion of said partially-fluorinated aldehydes from said product stream and using said separated portion of said partially-fluorinated aldehydes as a further reactant in said fluorinating step (b).

6. The method of claim 1, wherein the carbene reaction step (c) produces a product stream comprising a mixture of fluorinated aldehydes and a carbene-reaction product.

7. The method of claim 6, wherein the carbene-reaction product is selected from the group consisting of a highly-fluorinated ketone, a highly-fluorinated alkene and a mixture of a highly fluorinated ketone and a highly-fluorinated alkene.

8. The method of claim 7, further comprising the steps of separating at least a portion of said fluorinated aldehydes from said product stream and using said separated portion of said fluorinated aldehydes as a further reactant in said carbene reaction step (c).

9. The method of claim 1, wherein the reduction step (d) produces a product stream comprising a mixture of hydrofluorocarbons and a carbene-reaction product.

10. The method of claim 9, further comprising the steps of separating at least a portion of said carbene reaction product from said product stream and using said separated portion of said carbene reaction product as a further reactant in said reduction step (d).

11. The method of claim 1, wherein the chlorination step (a) comprises chlorinating a compound having the formula (I) as follows:

$$H_aX_bC\text{—}C(O)\text{—}H \qquad (I)$$

wherein a+b=3 and each X is independently selected from the group of halogens or other chemical moieties replaceable by chlorine.

12. The method of claim 11, wherein the chlorination step (a) comprises chlorinating a compound in which b is either 0 or 1.

13. The method of claim 12, wherein said compound is acetaldehyde.

14. The method of claim 1 wherein the fluorination step (b) comprises fluorinating a fully-chlorinated aldehyde to produce a fully-fluorinated aldehyde.

15. The method of claim 14 wherein the chlorination step (a) comprises chlorinating a compound having the formula (I) follows:

$$H_aX_bC\text{—}C(O)\text{—}H \qquad (I)$$

wherein a+b=3 and each X is independently selected from the group of halogens or other chemical moieties replaceable by chlorine, to produce a fully-chlorinated aldehyde.

16. The method of claim 15, wherein the chlorination step (a) comprises chlorinating a compound in which b is either 0 or 1.

17. The method of claim 16, wherein said compound is acetaldehyde.

18. The method of claim 17, wherein the carbene reaction step (c) comprises reacting said fully-fluorinated aldehyde with difluorocarbene to form a $C_3$ carbene reaction product.

19. The method of claim 18, wherein the reduction step (d) comprises reducing said $C_3$ carbene reaction product to form a $C_3$ hydrofluorocarbon.

20. The method of claim 1, wherein said hydrofluorocarbon comprises 1,1,1,3,3-pentafluoropropane and, said chlorinating step (a) comprises chlorinating acetaldehyde to produce trichloroacetaldehyde, said fluorinating step (b) comprises fluorinating said trichloroacetaldehyde to produce trifluoroacetaldehyde, said carbene reaction step (c) comprises reacting said trifluoroacetaldehyde to produce a mixture of pentafluoroacetone and pentafluoropropene, and said reducing step (d) comprises reducing said mixture of pentafluoroacetone and pentafluoropropene to produce 1,1,1,3,3-pentafluoropropane.

21. The method of claim 20, wherein said chlorinating step (a) further comprises reacting said acetaldehyde with an with a chlorinating agent to produce trichloroacetaldehyde.

22. The method of claim 21, wherein said chlorinating agent is selected from the group consisting of elemental chlorine, elemental chlorine diluted with inert gas, metallic chlorides, hydrochloric acid, hydrochloric acid and oxygen mixtures, hydrochloric acid and air mixtures, hypochlorides, and mixtures thereof.

23. The method of claim 22, wherein said chlorinating agent is elemental chlorine.

24. The method of claim 20, wherein said fluorinating step (b) further comprises reacting said trichloroacetaldehyde with an with a fluorinating agent to produce trifluoroacetaldehyde.

25. The method of claim 24, wherein said fluorinating agent is selected from the group consisting of substantially anhydrous hydrogen fluoride, aqueous hydrogen fluoride, metal fluorides, halogen fluorides, elemental fluorine, sulfur fluorides, and mixtures thereof.

26. The method of claim 25, wherein said fluorinating agent is substantially anhydrous fluoride.

27. The method of claim 20, wherein said carbene reaction step (c) further comprises reacting said trifluoroacetaldehyde with an with a difluorocarbene agent to produce a mixture of pentafluoroacetone and pentafluoropropene.

28. The method of claim 27, wherein said difluorocarbene agent is selected from the group consisting of chlorodifluoromethane, trifluoromethane, and mixtures thereof.

29. The method of claim 28, wherein said difluorocarbene agent is chlorodifluoromethane.

30. A method for the preparation of a hydrofluorocarbon comprising the steps of:
(a) chlorinating an aldehyde to produce a chlorinated aldehyde;
(b) fluorinating said chlorinated aldehyde to produce a fluorinated aldehyde; and
(c) converting said fluorinated aldehyde to a hydrofluorocarbon.

31. The method of claim 30, wherein the chlorination step (a) produces a product stream comprising a mixture of fully-chlorinated aldehyde and partially-chlorinated aldehydes.

32. The method of claim 31, further comprising the steps of separating at least a portion of said partially-chlorinated aldehydes from said product stream and recycling said separated portion of said partially-chlorinated aldehydes to said chlorinating step (a).

33. The method of claim 30, wherein the chlorination step (a) comprises chlorinating a compound having the formula (I) as follows:

$$H_aX_bC-C(O)-H \qquad (I)$$

wherein a+b=3 and each X is independently selected from the group of halogens or other chemical moieties replaceable by chlorine, to produce a fully-chlorinated aldehyde.

34. A method for the preparation of a hydrofluorocarbon comprising the steps of:
(a) chlorinating an aldehyde to produce a chlorinated aldehyde;
(b) converting said chlorinated aldehyde to a carbene reaction product; and
(d) reducing said carbene reaction product to produce a hydrofluorocarbon.

35. The method of claim 34, wherein the chlorination step (a) produces a product stream comprising a mixture of fully-chlorinated aldehyde and partially-chlorinated aldehydes.

36. The method of claim 35, further comprising the step of separating at least a portion of said partially-chlorinated aldehydes from said product stream.

37. The method of claim 34, wherein the chlorination step (a) comprises chlorinating a compound having the formula (I) as follows:

$$H_aX_bC-C(O)-H \qquad (I)$$

wherein a+b=3 and each X is independently selected from the group of halogens or other chemical moieties replaceable by chlorine, to produce a fully chlorinated aldehyde.

* * * * *